United States Patent [19]

Cuscurida

[11] Patent Number: 4,535,189

[45] Date of Patent: Aug. 13, 1985

[54] POLYOL PURIFICATION PROCESS

[75] Inventor: Michael Cuscurida, Austin, Tex.

[73] Assignee: Texaco Inc., White Plains, N.Y.

[21] Appl. No.: 591,703

[22] Filed: Mar. 21, 1984

[51] Int. Cl.$^3$ .............................................. C07C 41/03
[52] U.S. Cl. ................................... 568/620; 568/618; 568/619; 568/621; 568/678; 568/680
[58] Field of Search ............... 568/618, 619, 620, 621, 568/678, 680

[56] References Cited

U.S. PATENT DOCUMENTS

| | | | |
|---|---|---|---|
| 3,000,963 | 9/1961 | Speranza et al. | 260/615 |
| 3,030,426 | 4/1962 | Moseley et al. | 568/618 |
| 3,715,402 | 2/1973 | Louvar et al. | 260/613 B |
| 4,122,035 | 10/1978 | Cislo | 568/620 |
| 4,137,398 | 1/1979 | Muzzio | 568/620 |

OTHER PUBLICATIONS

Kirk–Othmer, Encyclopedia of Chemical Technology 2nd ed., vol. 9, (1966) pp. 268, 274.

*Primary Examiner*—Howard T. Mars
*Attorney, Agent, or Firm*—Jack H. Park; Kenneth R. Priem

[57] ABSTRACT

The filter cake formed by the filtering of a alkylene oxide polymer during the refining of the same contains a minor amount of alkylene oxide polymer which can be recovered therefrom by treating the filter cake with a lower aliphatic alcohol or an aqueous solution of lower aliphatic alcohol. Methanol is the preferred lower aliphatic alcohol.

8 Claims, No Drawings

POLYOL PURIFICATION PROCESS

ENVIRONMENT OF THE INVENTION

1. Technical Field of the Invention

This invention relates to an improved method for the purification of polyols of the type prepared by reacting alkylene oxides containing 2 to 4 carbon atoms with an initiator under alkaline conditions. More particularly, this invention relates to an improved purification process wherein a filtration step is utilized as part of the purification sequence. It has been discovered in accordance with the present invention that in a process of this nature polyol that is occluded in the filter cake formed by the filtration step may be separately recovered therefrom by treating the filter cake with a lower aliphatic alcohol or an aqueous solution of such lower aliphatic alcohol.

2. Prior Art

This invention is an improvement over a process for the refining of crude alkylene oxide polymers of the type disclosed in Speranza et al. U.S. Pat. No. 3,000,963. This patent discloses a process wherein propylene oxide is reacted with an initiator under alkaline conditions to form a crude high molecular weight polymer which is thereafter refined. As part of the refining sequence, the polymer, after being neutralized, is filtered to remove insoluble components in the reaction mixture.

Another refining method is disclosed in Louvar et al. U.S. Pat. No. 3,715,402. In accordance with the refining method disclosed therein, the alkylene oxide polymer, in crude form, is mixed with water and an organic solvent which is immiscible in water and in which the polyol is soluble. An acid is added to this mixture and the resultant mixture is resolved, for example by centrifugation. The polyol is thereafter separated from the solvent in purified form. It is an important characteristic of this technique that the solvent have a density substantially different from water. Examples of suitable solvents that are mentioned include materials such as aliphatic hydrocarbons, halogenated aliphatic hydrocarbons and halogenated aromatic hydrocarbons.

BACKGROUND OF THE INVENTION

High molecular weight polymers such as those having molecular weights in the range of about 500 to about 10,000 of the type prepared by reacting alkylene oxides with an initiator are variously referred to as adducts, polyols, polyglycols, etc. These materials are widely employed in commerce as lubricants, emulsifiers, plasticizers, solvents, and raw materials for the manufacture of polyurethane foam.

Such polymers are frequently manufactured in comparatively large facilities, such as kettle facilities having an annual capacity of as much as one hundred million pounds per year of polymer, or more. When a purification sequence of the type disclosed in Speranza et al. U.S. Pat. No. 3,000,963 is used as part of the manufacturing process, a small amount of the high molecular weight polymer will be occluded in the solids that are trapped by the filter during the filtration step that is part of the process. This filter cake must be removed from time to time and is normally considered to be a waste product and a loss to the process. Moreover, it frequently represents a cost item in that the filter cake must be disposed of in an environmentally acceptable manner.

Although the amount of alkylene oxide polymer that is occluded in the filter cake is compartively small, in the order of about one percent or so of the total volume of the polymer manufactured, nevertheless, when one considers a plant having a capacity of one hundred million pounds per year, this represents a loss of one million pounds of potential product which must be disposed of not through sale and use, but rather, by burning or other techniques which are environmentally acceptable for the disposal of waste products from chemical plants.

SUMMARY OF THE INVENTION

It has been discovered in accordance with the present invention that the filter cake formed by the filtering of an alkylene oxide polymer such as a polymer having an average molecular weight of about 500 to about 10,000 during the refining of the same contains a minor amount of alkylene oxide polymer which can be recovered therefrom by treating the filter cake with a lower aliphatic alcohol or an aqueous solution of lower aliphatic alcohol. Methanol is the preferred lower aliphatic alcohol. Preferably, the filter cake is treated with an aqueous solution of lower aliphatic alcohol in which the polyol is soluble, such as an aqueous solution containing up to about 40 wt. % of water.

DETAILED DESCRIPTION OF THE INVENTION

Polymer Preparation

The starting materials for the present invention are $C_2$–$C_4$ alkylene oxides, i.e., ethylene oxide, propylene oxide, butylene oxide, an initiator which is reactive with the alkylene oxide, such as an initiator containing one or more hydroxyl groups such as an alcohol, a glycol, a triol, etc. Examples of suitable initiators include compounds such as methanol, ethanol, butanol, 2-ethylhexanol, etc.; glycols such as ethylene glycol, diethylene glycol, triethylene glycol, propylene glycol, dipropylene glycol, etc.; triols such as glycerol, trimethylol propane, trihydroxyhexane, etc.; tetrols such as pentaerythritol, etc.

The initiator is reacted in a suitable reaction vessel, such as a jacketed kettle containing temperature control means and an agitator together with appropriate feed lines and draw-off lines. The initiator is reacted with one or more alkylene oxides under alkaline conditions to form an alkylene oxide polymer. The reaction is suitably conducted at a temperature of about 80° to about 150° C. under a modestly elevated pressure. Examples of alkaline materials that can be used in the reaction include sodium hydroxide, potassium hydroxide and the corresponding hydrides and alkoxides.

It will be understood that the alkylene oxide polymer that is formed in this fashion may be a homopolymer or a copolymer or an interpolymer. When more than one alkylene oxide is used, they may be charged to the kettle in admixture to form a heteropolymer or sequentially to form a block polymer.

A preferred alkylene oxide is propylene oxide. In order to enhance the utility of the propylene oxide polymers for particular purposes, it is a frequent practice to include a minor amount of ethylene oxide in the propylene oxide polymer. The ethylene oxide may be added before the propylene oxide, after the propylene oxide, in admixture with the propylene oxide, or in a desired sequence of blocks of ethylene oxide and propylene oxide to thus provide a polymer of desired configuration.

In general, the polymers that are formed are polymers having the following formula:

$$R-[O-C_3H_6O)_n(C_2H_4O-_mH]_x$$

wherein R is hydrogen or an aliphatic organic residue resulting from the removal of 1 to 4 hydroxyl groups corresponding to the value of x, which may have a value of 1 to 4. The value of n may vary from about 4 to about 50 and m may have a value of from 0 to about 5.

Polymer Purification

When the desired alkylene oxide polymer, such as a propylene oxide polymer, has been formed in the reaction vessel, it will be present as the major component of a crude reaction mixture and must be further refined in order to be useable. This is accomplished in accordance with a process of the type disclosed in Speranza et al. U.S. Pat. No. 3,000,963, by neutralizing the reaction mixture with an appropriate inorganic acid or acid forming material.

Examples of acids and acid forming materials that can be utilized to neutralize the reaction mixture include materials such as sulfuric acid, phosphoric acid, acetic acid, oxalic acid, etc.

After neutralization, the product is removed from the reaction vessel through a draw-off line and filtered to provide a desired finished product. The filtration step is a conventional filtration step of the type wherein the crude reaction mixture is pumped or otherwise drained through a filter to remove solid materials. As a consequence, the filter must be cleaned from time to time by removing the filter cake that is formed. This again can be done in a conventional fashion. For example, the filter cake can be washed from the filter, scraped from the filter, etc. into an appropriate container or line for disposal.

In accordance with the present invention the filter cake is recovered from the filter cleansing step and further treated in a separate vessel, which may suitably be a kettle provided with an agitator, temperature control means and appropriate inlet lines and draw-off lines.

In accordance with the present invention the filter cake is mixed with agitation with a treating agent comprising a lower aliphatic alcohol such as methanol, ethanol, propanol, isobutanol, etc., and preferably an aqueous solution of such alcohol containing up to about 40 wt. % of water. The occluded polyol is selectively dissolved in the aliphatic alcohol as a result of this treatment. In general, from about 0.1 to about 10 parts by weight of treating agent is used for each part of filter cake, such as about 0.25 to about 5 parts and, more preferably, about 0.5 to about 2.5 parts.

Thereafter, the thus treated filter cake is again filtered to remove undissolved solids and the filtrate is treated in any appropriate manner (e.g., by distillation) in order to remove the water and alcohol. The resultant product is a polyol suitable for use in commerce.

In accordance with the preferred embodiment of the present invention, the lower aliphatic alcohol that is used is methanol, and the methanol is used in the form of an aqueous solution containing up to about 40 wt. % of water, such as an aqueous solution of methanol containing from about 60 to about 90 wt. % of methanol.

SPECIFIC EXAMPLES

EXAMPLE 1

This example illustrates the use of a 90 wt. % aqueous solution of methanol for the extraction of propylene oxide polymer from a filter cake. The filter cake was formed during commercial operations at a commercial facility wherein a 3500 molecular weight propylene oxide polymer containing about 14 wt. % of ethylene oxide was being manufactured. The filter cake contained acid salts, some propylene oxide polymer (polyol), filter aid, etc.

About 11.75 pounds of the thus obtained filter cake was charged to a five-gallon kettle together with about 12.5 pounds of a 10:1 by weight methanol-water solution. The mixture was stirred at 25° C. for 1 hour and filtered. The extract filtered clear. Thereafter, the polyol was recovered from the filtrate using conventional techniques, in this instance vacuum distillation, wherein the filtrate was stripped at a pressure of about 5 millimeters of mercury at a temperature of about 100° to 105° C. until no further liquid was removed overhead. The recovered polyol (7.79 pounds) had the following properties:

TABLE I

| Properties | Sample No. 5243-79 |
|---|---|
| Acid no., mg KOH/g | 0.046 |
| Hydroxyl no., mg KOH/g | 47.4 |
| Water, wt. % | 0.01 |
| Unsaturation, meq/g | 0.015 |
| pH in 10:6 isopropanol-water | 5.1 |
| Sodium, ppm | 0.1 |
| Potassium, ppm | 8.1 |
| Peroxide, ppm | 1.5 |

The polyol, as can be seen from Table I, is suitable for use in the manufacture of polyurethane foam.

EXAMPLE 2

This example will illustrate the use of methanol to extract polyol from the filter cake described in Example 1.

About 13.8 pounds of filter cake and about 12.1 pounds of methanol were charged to a five-gallon kettle. The mixture was then stirred for 1 hour at about 50° C. and filtered. The inside of the kettle was examined and heavy deposits had accumulated on the agitator and on the walls of the kettle. An additional 10 pounds of methanol was charged to the kettle in an attempt to loosen the solids. The kettle was then given a water wash to remove the remaining solids.

The filtrate cake from the above operations was vacuum stripped as in Example 1 at about 100° C. The finished product (9.61 pounds) had the following properties:

TABLE II

| Properties | Sample No. 5243-74 |
|---|---|
| Acid no., mg KOH/g | 0.038 |
| Hydroxyl no., mg KOH/g | 47.8 |
| Water, wt. % | 0.03 |
| Unsaturation, meq/g | 0.016 |
| pH in 10:6 isopropanol-water | 5.4 |
| Color, Pt—Co | 125–150 |
| Sodium, ppm | 0.5 |
| Potassium, ppm | 14.6 |

TABLE II-continued

| Properties | Sample No. 5243-74 |
|---|---|
| Peroxide, ppm | 1.7 |

Again, the properties listed in Table II demonstrate that the polyol is suitable for use as a raw material in the manufacture of polyurethane foam.

EXAMPLE 3

This example will illustrate the attempted use of liquid carbon dioxide to extract polyol from the filter cake. In this example, the filter cake is a filter cake obtained during a commercial operation for the production of a 3000 molecular weight propylene oxide adduct of glycerin wherein propylene oxide and ethylene oxide were reacted with the glycerin, the ethylene oxide constituting about 14 wt. % of the alkylene oxide mixture.

About 100 grams of the filter cake were charged to a one-liter stirred autoclave which was then closed. About 500 grams of liquid carbon dioxide was charged to the autoclave and the mixture was stirred and heated for 2 hours at about 70° C. A maximum pressure of about 1925 psig developed during this period. Stirring was then stopped and the mixture was allowed to stand for 1 hour. About 100 grams of material from the top phase of the mixture was bled into a preweighed evacuated bomb. The sample bomb was bled down through a water-filled flask. The water gained no weight after the bleed was completed, indicating that none of the polyol had been extracted by the carbon dioxide.

Discussion

As seen by the foregoing examples, the improved process of the present invention results in the recovery of useful propylene oxide polymers which would otherwise be lost from the manufacturing process as waste materials.

The treatment of the filter cake with the aliphatic alcohol or aqueous aliphatic alcohol solution may be conducted under mild conditions. It has been found that temperatures within the range of about 25° to 100° C. and pressures ranging from about atmospheric to about 100 psig can be used with good results.

In a preferred embodiment of the present invention, the propylene oxide polymer is a triol prepared by reacting an alkylene oxide component consisting of 100 to about 75 wt. % of propylene oxide and 0 to about 25 wt. % of ethylene oxide with a polyhydric alcohol having a functionality of 3. The amount of propylene oxide and ethylene oxide used are such as to provide a final triol having a molecular weight within the range of about 3000 to about 10,000 and a hydroxyl number within the range of about 15 to about 150. More preferably, the polyol will have a molecular weight within the range of about 3000 to about 7000 and a hydroxyl number of about 20 to about 80. Products of this nature are particularly useful as raw materials for the manufacture of flexible polyurethane foam.

It will be understood that the foregoing examples are given by way of illustration and not by way of limitation and that the scope of the present invention is defined solely by the appended claims.

What is claimed is:

1. In a method wherein a $C_2$-$C_4$ alkylene oxide is reacted with an initiator to form an alkylene oxide polymer under alkaline conditions in the presence of a hydroxide, hydride or alkoxide of sodium or potassium and wherein the alkylene oxide polymer is thereafter neutralized with an acid component comprising sulfuric acid, phosphoric acid, acetic acid or oxalic acid and then passed through a filter to obtain a final alkylene oxide polymer product, the improvement which comprises:
   (a) recovering filter cake resulting from the filtration step;
   (b) mixing said filter cake with a treating agent comprising a lower aliphatic alcohol containing from about 1 to 4 carbon atoms and also containing from 0 up to about 40 wt. % of water;
   (c) filtering said mixture; and
   (d) recovering additional alkylene oxide polymer from said filtrate from said second filtration step.

2. A method as in claim 1 wherein the alkylene oxide comprises propylene oxide and the treating agent comprises methanol.

3. In a method as in claim 1 wherein the initiator has a functionality of from about 1 to about 4 and wherein the initiator is reacted under alkaline conditions with an alkylene oxide component consisting of from 100 to about 75 wt. % of propylene oxide and from 0 to about 25 wt. % of ethylene oxide to form a propylene oxide polymer having a molecular weight of up to about 10,000, such product having the formula:

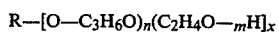

$$R-[O-C_3H_6O)_n(C_2H_4O-_mH]_x$$

wherein R is hydrogen or an aliphatic organic residue resulting from the removal of 1 to 4 hydroxyl groups corresponding to the value of x, wherein x has a value of 1 to 4, wherein n has a value from about 4 to about 50 and wherein m has a value of from 0 to about 5,
   (a) the improvement which comprises washing the filter cake obtained by the filtration of said product with an aqueous solution of methanol at a temperature within the range of about 25° to about 100° C. for a period of time within the range of from about 0.5 to about 5 hours;
   (b) thereafter refiltering said methanol filter cake mixture; and
   (c) recovering polyol from the filtrate from said second filtration step.

4. A method as in claim 3 wherein the filter cake is treated with an aqueous solution of methanol containing from about 10 to about 40 wt. % of water.

5. In a method for the manufacture of a polyol useful as a raw material in the making of polyurethane foam and wherein a trifunctional initiator containing three hydroxyl groups is reacted with an alkylene oxide component consisting of 100 to about 75 wt. % of propylene oxide and 0 to about 25 wt. % of ethylene oxide under alkaline conditions in the presence of a catalytic amount of a hydroxide, hydride or alkoxide of sodium or potassium to provide a polyoxy alkylene triol having a molecular weight within the range of about 1000 to 10,000 and a hydroxyl number within the range of about 15 to 150, and wherein the triol formed as a result of said reaction is neutralized with sulfuric, phosphoric, acetic or oxalic acid, filtered, and recovered, the improvement which comprises:
   (a) separately recovering the filter cake formed as a result of the filtration of said triol;
   (b) mixing from about 0.1 to about 10 parts by weight of filter cake with a treating agent comprising an aqueous solution of methanol containing from about 10 to about 40 wt. % of water at a temperature within the range of about 25° to about 100° C. for a period of time within the range of about 0.5 to about 5 hours;
(c) filtering said methanol filter cake mixture in a second filtering operation; and
(d) recovering additional triol from said filtrate from said second filtration step.

6. A method as in claim 5 wherein the filter cake is mixed with about 0.5 to about 2.5 parts by weight of said treating agent per part of said filter cake.

7. In a method for the manufacture of a polyol useful as a raw material in the making of polyurethane foam and wherein an initiator containing one to four hydroxyl groups is reacted with an alkylene oxide component consisting of 100 to about 75 wt. % of propylene oxide and 0 to about 25 wt. % of ethylene oxide under alkaline conditions in the presence of a hydroxide, hydride or alkoxide of sodium or potassium to provide a polyoxy alkylene polyol having a molecular weight within the range of about 1000 to 10,000 and a hydroxyl number within the range of about 15 to 150, and wherein the polyol formed as a result of said reaction is neutralized with an acid component composed of sulfuric acid, phosphoric acid, acetic acid or oxalic acid, filtered, and recovered, the improvement which consists of:
(a) separately recovering the filter cake formed as a result of the filtration of said polyol;
(b) mixing from about 0.1 to about 10 parts by weight of filter cake with a treating agent consisting of an aqueous solution of methanol containing from about 10 to about 40 wt. % of water at a temperature within the range of about 25° to about 100° C. for a period of time within the range of about 0.5 to about 5 hours;
(c) filtering said methanol filter cake mixture in a second filtering operation; and
(d) recovering additional polyol from said filtrate from said second filtration step.

8. A method as in claim 7, wherein the filter cake is mixed with about 0.5 to about 2.5 parts by weight of said treating agent per part of said filter cake.

* * * * *